United States Patent [19]

Garçonnet

[11] Patent Number: 5,766,715
[45] Date of Patent: Jun. 16, 1998

[54] COMPACT DISPOSABLE PACKING THAT FORMS A KIT

[75] Inventor: Michel Garçonnet, Meulers, 76510, St Nicolas d'Aliermont, France

[73] Assignees: Michel Garçonnet; Claudine Marie-Christine Garçonnet; Armelle Annick Garçonnet, all of St. Nicolas d'Aliermont; Corinne Madeleine Gisèle Garçonnect, Criquetot l'Esneval, all of France

[21] Appl. No.: 630,423

[22] Filed: Apr. 3, 1996

[30] Foreign Application Priority Data

Apr. 10, 1995 [FR] France ................. 95 04243

[51] Int. Cl.[6] ............................ A61F 17/00
[52] U.S. Cl. ............... 428/40.1; 206/570; 206/572; 206/582; 206/803; 428/42.1; 428/43; 428/68; 428/71; 428/74; 428/192; 428/194; 428/201; 428/202; 428/203
[58] Field of Search ................... 428/40.1, 192, 428/194, 68, 71, 74, 43, 201, 202, 203, 42.1; 206/570, 572, 582, 803

[56] References Cited

U.S. PATENT DOCUMENTS 2,377,117  3/1945  Watkins ................. 206/38
2,391,094  12/1945  Karg .................... 206/570
3,565,075  2/1971  Jerry .................... 128/268
3,748,098  7/1973  Dutch ................... 206/803
4,808,172  2/1989  Murata .................. 604/306

FOREIGN PATENT DOCUMENTS 1111282   9/1954  France .
1202856   1/1958  France .
2 255 224  12/1974  France .
1 087 758  8/1960  Germany .

Primary Examiner—Nasser Ahmad
Attorney, Agent, or Firm—Browdy and Neimark

[57] ABSTRACT

The compact disposable packing for kit that contains aiding means which are secured from any contamination comprises a back plate made of plastic material. The back plate is covered with a sheet that forms a reservoir which opens in a small duct comprising a breakage incipient area. The sheet is itself covered with a hood that delimits a housing for a member like a gauze and similar. The plate, the sheet and the hood are tightly assembled and sealed, and the breakage incipient area is arranged so that the small duct is broken in the housing upon bending the back plate for bringing a fluid contained in the reservoir to impregnate the member.

11 Claims, 2 Drawing Sheets

COMPACT DISPOSABLE PACKING THAT FORMS A KIT

FIELD OF THE INVENTION

The present invention relates to a multi purpose kit enabling to keep under a small space and secured from air a plurality of products having thereafter to be used together or successively for carrying into effect various actions.

According to the invention, liquid, pasty and/or solid products are conditioned in a packing and are made usable at any time.

The invention assures that hands of a user will not come into contact with some of the products, that these products are always secured from comtaminations risking to modify properties of the products, and that some of the products so contained are brought together into contact before opening the kit while they remain isolated from other products to which it is possible ultimately to have access. The invention also provides that a plurality of kits are connected together for the selling and maintenance thereof while they are used successively.

The present invention finds a particularly suitable application in the making of first aid dressings placed in a disposable packing and able to be used in any place both by experienced people and by the general public. The invention can samely be suitable for the conditioning of food products, cosmetic products, cleaning products, and the like.

BACKGROUND OF THE INVENTION

Prior art has already disclosed small cases that form kits for first aid interventions.

In this respect, FR-A-1 202 852 has disclosed a cover or pocket that contains a liquid, such as a disinfecting liquid as well as an applicator for example a cotton-wool pad, a portion that contains the liquid being spaced apart, from a portion that contains the cotton-wool pad, by a closing member which can be ejected by pressure. The small cover or pocket comprises one side with a breakage incipient area that can be torn to gain access to the pad which can be taken by the user with his/her fingers.

The known device protects both the liquid and the pad as long as this device is not open, but the device necessitates that the pad, once impregnated with the liquid, is taken with fingers, which can cause a contamination of the pad by various external agents.

U.S. Pat. No. 2,377,117 discloses a first aid kit that is similar to a fountain-pen within which is placed a supply of a liquid contained in a reservoir closed by a spongy like tip. A roll of a self-adhesive bandage is, moreover, also arranged within the body of the pen shaped kit.

In the above known embodiment, the spongy-like tip can obviously be submitted to contamination, and the same is true for the wrapped bandage.

U.S. Pat. No. 3,964,604 discloses a flexible packaging bag that delimits a mixing chamber and at least one reservoir chamber which can communicate together through an opening of a breakage area.

This publication does not show any elements for constituting a dressing so that the products able to be mixed together cannot prevent a possible contamination of a pad of cotton-wool, gauze or other material having to be impregnated. DE-C-1 087 758 discloses a roller for delimiting successive segments that respectively contain spongy-like pads, and flasks that contain impregnation liquids. In this case also, at least the spongy-like pads can be submitted to contaminations.

FR-A-1 111 282 discloses a small case that delimits two compartments, one compartment for an ampoule that contains a disinfecting liquid and another compartment for a self-adhesive dressing. When the small case is open, both the ampoule and the dressing must be taken by the user with his/her fingers, which generates a risk of contamination at least of the dressing.

PURPOSE OF THE INVENTION

The object of the present invention is particularly a new packing that forms a kit for first aid dressing in which both the pad and the impregnated liquid are permanently kept secured from any contamination, impregnation of the pad being thereafter made without manual contact with the pad and with the liquid, and the impregnated pad being usable also without the fingers of the user coming into contact with the impregnated pad so that the pad is secured from any contamination even if the user has not been in a position to wash and disinfect his/her hands, contrary to what is done by a doctor in a medical room.

Moreover, the invention enables, after a wound has been cleaned by means of the sterile pad that is impregnated with a treating product, to position a protecting dressing without this protecting dressing having been into contact with fingers of a user.

Therefore, both the cleaning of a wound and the positioning of a dressing can be made without any risk of contamination.

SUMMARY OF THE INVENTION

According to the invention, the compact disposable packing for kit that contains first aid means which are secured from any contamination is characterized in that it comprises a back plate of plastic material covered with a sheet that forms a reservoir which opens in a small duct comprising a breakage incipient area. The sheet is itself covered with a hood that delimits a housing for a member like a gauze and similar, the plate. The sheet and the hood that delimit the housing are tightly assembled and sealed. The breakage incipient area is arranged so that a small duct is broken in the housing of the hood upon bending the back plate. This brings a fluid contained in the reservoir to impregnate the member placed in the housing of the hood.

According to another important feature of the invention, the back plate is provided, on a face opposed to that which is covered by the sheet, with a bag which is formed by a self-adhesive film,the self-adhesive film being itself covered with a self-adhesive sheet for protecting a covering means of the dressing type which is accessible by peeling off the self-adhesive sheet, with directions of use being carried by the self-adhesive sheet.

Various other features of the invention will moreover be revealed from the following detailed disclosure.

BRIEF DESCRIPTION OF THE DRAWINGS

An embodiment of the invention is shown, as a non limitative example, in the accompanying drawings, wherein.

DETAILED DESCRIPTION OF THE INVENTION

Figure 1:
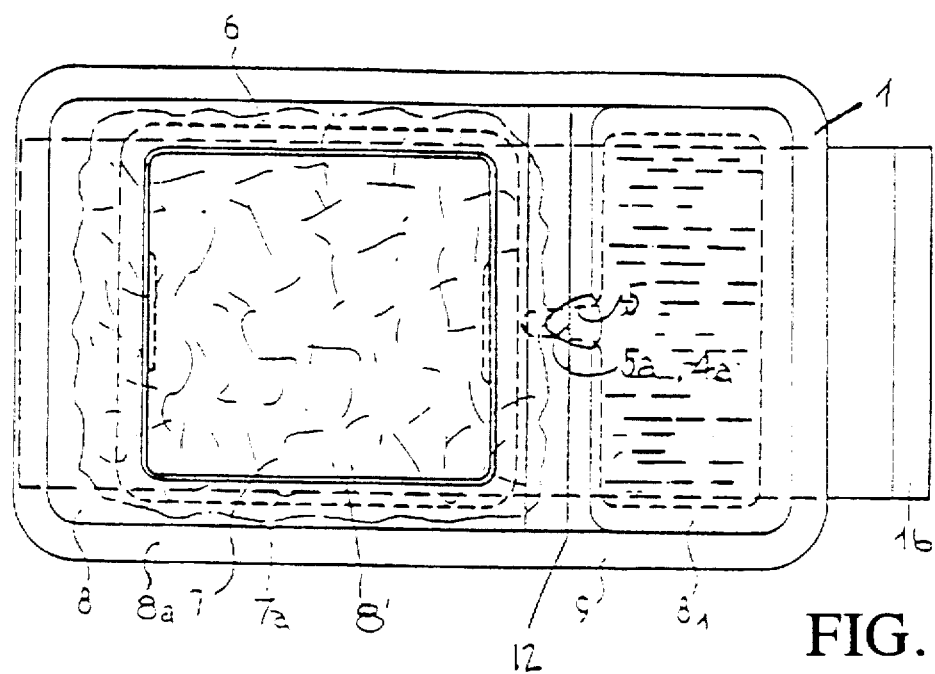
FIG. 1 is a top view of a complete packing that forms a kit.
Figure 2:
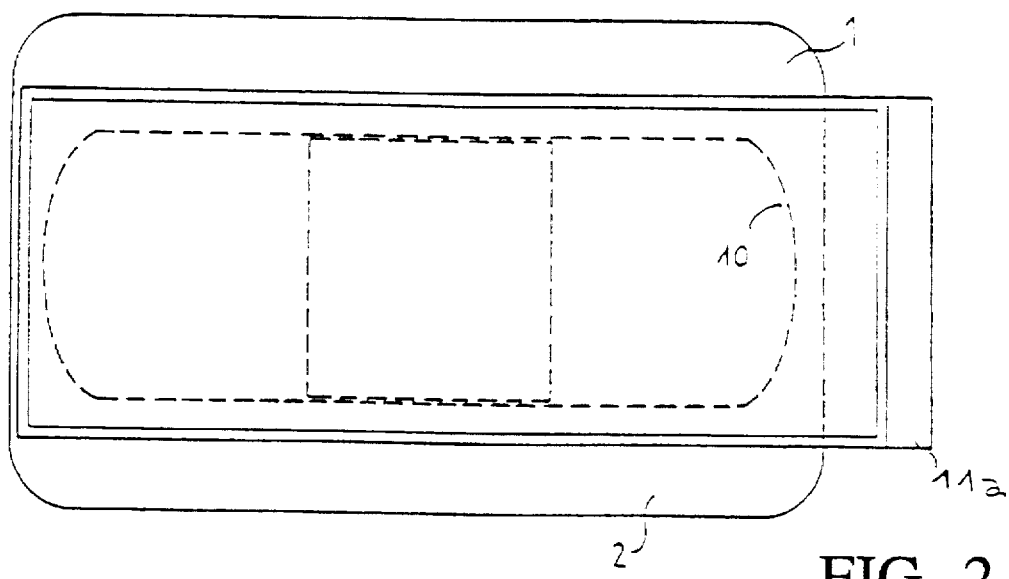
FIG. 2 is a bottom view of the kit of FIG. 1.

In the following disclosure, the kit is described as a packing for first aid dressing, without however been limited to such an embodiment.

In the drawings, a flexible film 1a of a bag 1 having a generally rectangular shape is covered with a coating of a synthetic adhesive 2 on at least its face that is upwardly directed.

The adhesive coated surface of the flexible film 1a is made adhering with a back plate 3. The part 3a of the back plate 3 which is shown at right hand of the drawing, is opposite to a reservoir 4a containing an active product which generally is a liquid or a more or less viscous fluid.

A plurality of disinfecting products can be used as the active product.

The reservoir 4a is delimited by a sheet 4 made of a rigid plastic material which is compatible with that forming the back plate 3 for enabling a tight connection therewith by soldering or any other suitable means.

The reservoir 4a is extended by a small duct 5 formed as the reservoir 4a by an upper part of the back plate 3 that forms the bottom portion of the reservoir 4a.

The small duct 5 is provided, in a part of its wall formed by the sheet 4, with a breakage incipient area 5a for facilitating an opening of the small duct 5.

A pad 6 or other applicator, made of gauze or an other product which can be shredded or is able to be rolled, pleated or bent in any other appropriate shape, is arranged on a top portion of the back plate 3.

The pad 6, as well as both the reservoir 4a and the small duct 5 are covered with a hood 8 of a clear plastic material preferably of a same kind as that forming the sheet 4, this hood 8 delimiting a frame 8a covering a periphery of the sheet 4.

The hood 8 delimits a housing $8_1$ for covering the reservoir 4a, and a housing $8_2$ for covering the pad 6 separated by score line 12.

Figure 3:
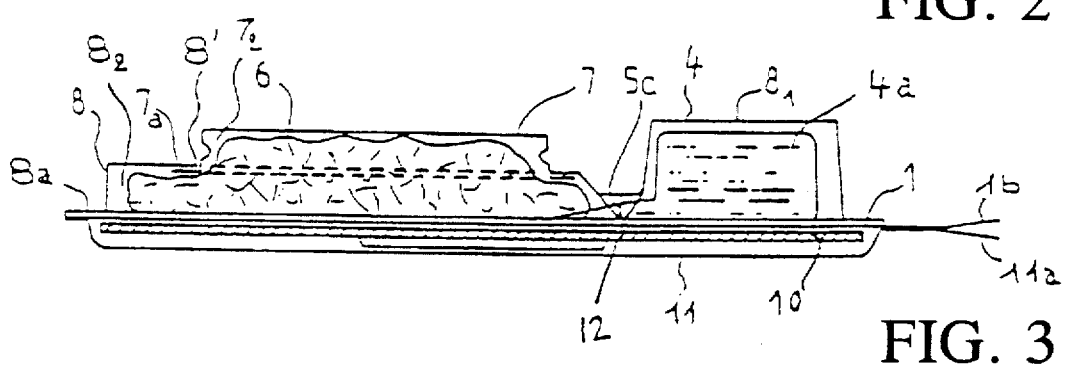
FIG. 3 is a side view of the kit.

As shown in the drawings, it is advantageous that the housing $8_2$ has an opening 8' for a plug 7 having an edge 7a bearing on a bottom portion of an upper part of the housing $8_2$, as illustrated in FIG. 3.

The plug 7 is a hollow plug and is filled by the pad 6 which maintains the edge 7a on the lower wall of the housing $8_2$, thereby ensuring a suitable tightness between these two members.

Figure 4:
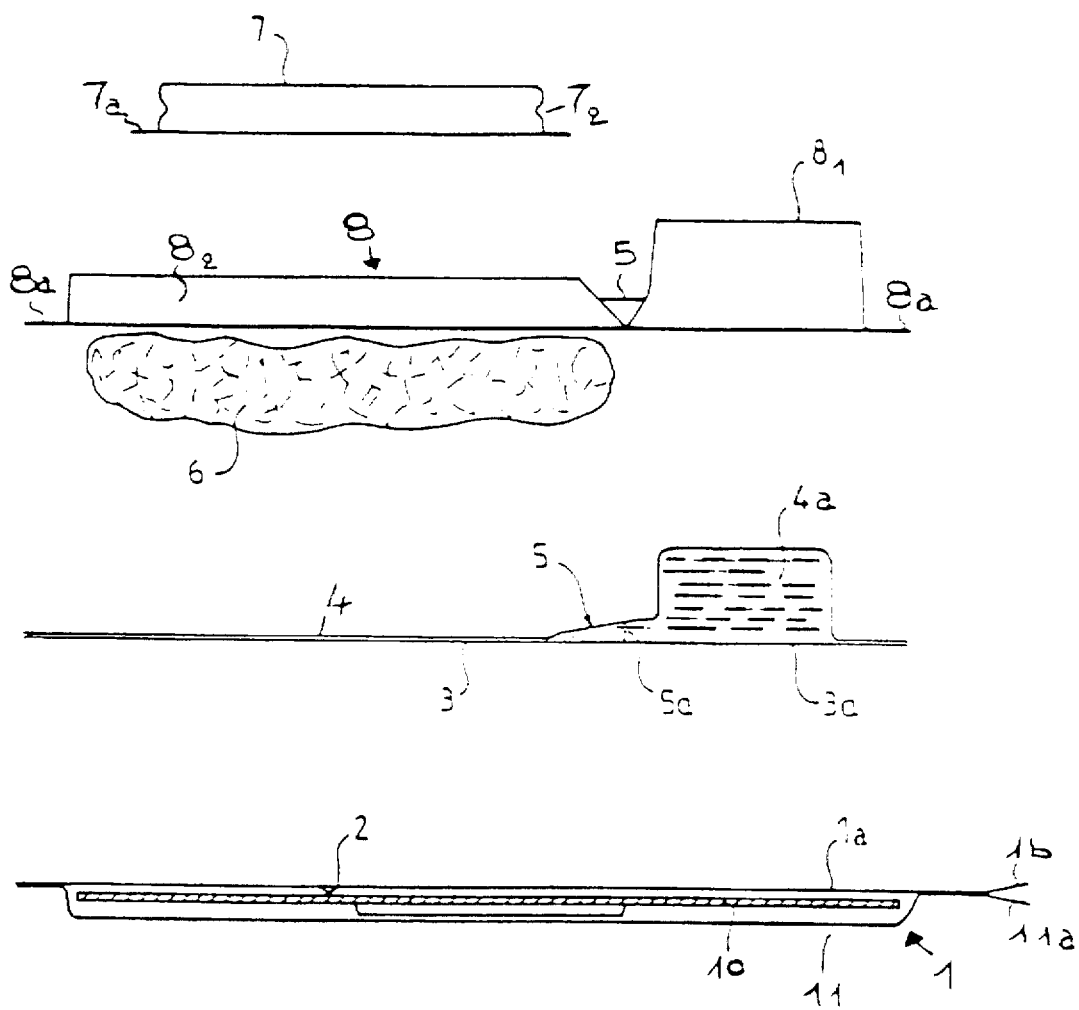
FIG. 4 is an exploded side view of the kit.

As this is diagrammatically illustrated in FIGS. 3 and 4, the plug 7 has possibly a bellows shaped side wall $7_2$ for permitting a possible deformation thereof.

The width of the edge 7a, of the plug 7, which is made in a flexible plastic material similar to that of the hood 8, is small for enabling a possible extraction of this plug, as this is explained hereinafter.

It is also possible, without departing from the scope of the invention, that the plug 7 is formed integrally with the wall of the housing $8_2$, and that the edge 7a is substituted by a breakage incipient area similar to the breakage incipient area 5a.

It is also possible, for ensuring a full tightness between the wall of the housing $8_2$ and the plug 7, that the edge 7a is connected to the wall of the housing $8_2$ by a seal tightness material, such as a wax material.

The housing $8_1$ which covers the reservoir 4a is advantageously used for showing graphical signs that are printed on an inner wall of the housing $8_1$. These graphical signs can for example give an information about a reference of a manufacturing batch, a time limitation date or other information which are thus made indelebile since they are not accessible from the outside.

As this is shown from the above description, the various members as above described, except the pad 6, are made of plastic material, this plastic material being preferably a clear plastic material at least for the making of the hood 8 in order that the above mentioned graphical signs are clearly readable and that the pad 6 as well as the product contained in the reservoir 4a can easily be seen.

The connection between the hood 8, the back plate 3 and the sheet 4 is made by glueing or by soldering, or by any other suitable means appropriate to the art of the material used for making these parts.

The bag 1 is prepared separately by placing, in a known manner, a dressing 10 or an other covering means on the flexible film 1a and by covering this dressing and the flexible film 1a with a self-adhesive sheet 11, the visible lower face of which being provided with information about directions of use.

Preferably, both the flexible film 1a and the self-adhesive sheet 11 covering the dressing 10 will project beyond the back plate 3 as shown at 1b and 11a in the drawings.

When it is desired to use the dressing, the small duct 5 is broken along the breakage incipient area 5a by bending the back plate 3 along score line 12, the sheet 4 and the hood 8 between the housings $8_1$ and $8_2$, which makes the liquid or semi-liquid active product contained in the reservoir 4a impregnate the pad 6. Flowing of the active product is accelerated by pressing the reservoir 4a between fingers.

When the pad 6 is impregnated, the plug 7 is extracted by pressing it between fingers, which withdraws at the same time the pad 6 which can be used for cleaning and disinfecting a wound without the pad being into contact with fingers and, consequently, without this pad having been submitted to any contamination since it remains within the plug 7. Maintaining the pad 6 within the plug 7 is still improved when the plug 7 comprises a bellows shaped edge $7_2$.

A similar use of the pad 6 maintained within the plug 7 is obtained when a pre-breakage line is provided in the wall of the housing $8_2$.

After a cleaning of the wound, the self-adhesive sheet 11 of the bag 1 is peeled off, which permits an application of the dressing 10 on the wound without the dressing 10 having been itself into contact with fingers of a user.

This obviates also any contamination of the dressing 10.

The ends 1b, 11a of the sheets that constitute the bag 1 facilitate a handling of the dressing, and samely the glueing of the flexible film 1a on the back plate 3 facilitates the handling of the dressing, this back plate 3 forming a relatively rigid support for the bag 1 as long as the sheet 11 is not peeled off.

The invention is not restricted to the embodiment shown and described in detail since various modifications thereof can be applied thereto without departing from its scope as shown in the appendant claims.

What I claim is:

1. A compact disposable packing kit having first aid means which are secured from any contamination, comprising a back plate (3) made of plastic material, said back plate being covered with a sheet (4) that forms a reservoir (4a) having a disinfecting fluid therein, said reservoir openable through a small duct (5) having a breakage incipient area (5a), said sheet (4) being covered with a hood (8) having a score line that delimits a housing ($8_2$) from the reservoir, said housing ($8_2$) having an applicator member therein, the plate (3), the sheet (4) and the hood (8) being tightly assembled and sealed, wherein said breakage incipient area (5a) is located so that when said small duct (5) is broken upon bending said back plate (3) along the score line, the disinfecting fluid contained in said reservoir (4a) impregnates said applicator member (6) in said housing ($8_2$), wherein said housing ($8_2$) has an upper wall provided with a plug (7) separable through said housing for engaging said applicator member (6) after being impregnated.

2. The packing as set forth in claim 1, wherein said hood (8) delimits a second housing ($8_1$) covering said reservoir (4a) formed between said sheet (4) and said back plate (3).

3. The packing as set forth in claim 2, wherein an inner wall of a portion of said hood (8) that delimits said housing ($8_1$) comprises graphical signs.

4. The packing as set forth in claim 1, wherein said back plate (3) is provided, on a face opposed to that which is covered by said sheet (4), with a bag (1) which is formed by a self-adhesive film (1a), said self-adhesive film being covered with a self-adhesive sheet (11) for protecting a covering means which is accessible by peeling off said self-adhesive sheet (11), with directions of use being carried by said self-adhesive sheet (11).

5. The packing as set forth in claim 4, wherein both said self-adhesive flexible film (1a) and said self-adhesive sheet (11) are provided with ends (1b, 11b), with said ends projecting beyond a frame (8a) delimited by said back plate (3), said sheet (4) and said hood (8) for sealing thereof by means of a fixing component.

6. The packing as set forth in claim 1, wherein said plug (7) is separably maintained on said upper wall by an edge (7a).

7. The packing as set forth in claim 1, wherein said plug (7) is formed by said upper wall of said housing, and wherein a breakage incipient area is formed around said plug (7) to permit said plug to be separated from said housing with said applicator member.

8. The packing as set forth in claim 1, wherein said plug has bellows shaped side walls to enhance engagement of said applicator member.

9. The packing as set forth in claim 1, wherein at least the hood (8) is made of a clear plastic material.

10. The packing as set forth in claim 5, wherein said fixing component is a glue.

11. The packing as set forth in claim 5, wherein said fixing component is a solder.

\* \* \* \* \*